(12) United States Patent
Sierra et al.

(10) Patent No.: US 7,943,797 B2
(45) Date of Patent: May 17, 2011

(54) PRODUCTS FOR THE TREATMENT OF THE IRON CHLOROSIS

(75) Inventors: Miguel A. Sierra, Madrid (ES); Mar Gomez-Gallego, Madrid (ES); Juan J. Lucena, Madrid (ES); Sonia Garcia-Marco, Madrid (ES); Rosa Escudero, Madrid (ES)

(73) Assignee: Tradecorp, S.A., Madrid (ES)

( * ) Notice: Subject to any disclaimer, the term of this patent is extended or adjusted under 35 U.S.C. 154(b) by 109 days.

(21) Appl. No.: 12/520,450

(22) PCT Filed: Dec. 20, 2007

(86) PCT No.: PCT/EP2007/064370
§ 371 (c)(1),
(2), (4) Date: Jun. 19, 2009

(87) PCT Pub. No.: WO2008/077897
PCT Pub. Date: Jul. 3, 2008

(65) Prior Publication Data
US 2010/0022394 A1    Jan. 28, 2010

(30) Foreign Application Priority Data

Dec. 22, 2006 (EP) .................................. 06127041

(51) Int. Cl.
*C07C 229/00* (2006.01)
(52) U.S. Cl. ...................................................... 562/433
(58) Field of Classification Search .................. None
See application file for complete search history.

(56) References Cited

U.S. PATENT DOCUMENTS
5,679,704 A  10/1997 Schonafinger et al.

FOREIGN PATENT DOCUMENTS
DE      3329028       2/1985
WO      9530651       11/1995
WO      2005/095305   10/2005
WO      WO-2006045852  4/2006

OTHER PUBLICATIONS

Sierra et al. (Dalton Transactions, 2004, 3741-3747).*
European Search Report EPO Application No. 061270419.-2103 of May 7, 2007.
Notification of Transmittal of the International Search Report and the Written Opinion of the International Searching Authority PCT/EP2007/064370 of Apr. 23, 2008.
Pecorraro et al. Stepwise Metal-Assisted Oxidative Decarboxylation of Vanadium (V) Ethylenebis (o-hydroxyphenyl) glycine). Isolation of a possible intermediate J. Am. AChem. Soc., vol. 106, No. 11, 1984, pp. 3360-3362.
Xinhua Li et al. "Stepwise, Metal-assisted Decarboxylation promoted by Manganese: Reactivity Relationship between Manganese and Vanadium" Inorg. Chem., vol. 28, 1989, pp. 3403-3410.
Gómez-Gallego et al. Understanding of the Mode of Action of Fe iii-EDDHA as Iron Chlorosis Corrector Based on Its Photochemical and Redox Behaviour (c.f. Chem.Eur.J. 2005, 11, 5997-6005).
Yunta et al. "Theoretical Speciation of Ethylenediamine-N-(o-hydroxyphenylacetic)-N-(p-hydroxyphenylacetic) Acid (o, p-EDDHA) in Agronomic Conditions" Journal of Agricultural and Food Chemistry, 2003, 51, 5391-5399.
Lucena, J.J. Chapter 5 "Synthetic Iron Chelates To Correct Iron Deficiency In Plants" Chapter 5, In Iron Nutrition in Plants and Rhizospheric Microorganism 2006, pp. 103-127, Springer-Verlag Academic Publishers. Chem. Eur. J. 2005, 11, 5997.
European Office Action dated May 21, 2010 from corresponding European Patent Application No. 07 857 989.3-2103.

* cited by examiner

*Primary Examiner* — Daniel M Sullivan
*Assistant Examiner* — Jennifer C Sawyer
(74) *Attorney, Agent, or Firm* — Robert Mlotkowski; Safran & Cole P.C.

(57) ABSTRACT

The present invention consists on the synthesis of new products for the treatment of the iron chlorosis. These products may have improved properties regarding the currently known treatments. The new products are non-symmetrical ethylene diamino hydroxyphenyl acetic acid derivatives possessing only five coordination sites able to chelate metals.

16 Claims, 3 Drawing Sheets

PRODUCTS FOR THE TREATMENT OF THE IRON CHLOROSIS

CROSS-REFERENCE TO RELATED APPLICATIONS

The present Application is a national phase of PCT/EP2007/064370 filed on Dec. 20, 2007 ("PCT Application"), which claims priority from European Application No. EP 06127041.9 filed on Dec. 22, 2006, both of which are hereby incorporated by reference in their entirety into the present Application, including any amendments made in the PCT application during the international phase.

FIELD OF THE INVENTION

This invention relates to new non-symmetrical ethylene diamino hydroxyphenyl acetic acid derivatives. These products are useful for the treatment of iron chlorosis.

BACKGROUND ART

Iron chlorosis is a nutritional plant disorder which results in a decrease in the amount of chlorophyll and in the yellowing or whitening of normally green plant tissue. It is a widespread problem in agriculture that affects the development of many crops provoking a decrease yield.

Attempts have long been made to correct this iron deficiency by feeding the plants with iron in assimilable form, originally in the form of ferric salts. Ferric salts act to a certain extent by foliar penetration, but are substantially ineffectual when used for soil treatment. It is through the roots that the penetration of iron is at its most effective in controlling chlorosis. In this connection, simple iron salts have been replaced by iron chelates which are hydrosoluble complexes consisting of an iron atom attached to several points of a single organic molecule known as chelates or co-ordinates. Some of these products known as hexadentates, such as complexes of iron with ethylene diamine tetracetic acid (EDTA) or with diethylene triamine pentacetic acid (DTPA) or with N,N'-ethylene-bis-(hydroxyphenyl)glycines (EDDHA), have been successfully used against chlorosis.

N,N'-ethylene-bis(2-hydroxyphenyl)glycine (o,o-EDDHA) is often described as one of the most favorable compounds for complexing metals, and being most suitable for the use as a plant nutrient or fertilizer because the complexation affinity to iron is particularly strong. The ferric chelate of o,o-EDDHA shows a coordination number of 6 and is widely used for agrochemical purposes as a plant nutrient or plant fertilizer, and for the treatment of chlorosis in crop plants.

The N,N'-ethylene-(2-hydroxyphenyl)-glycinyl-(4-hydroxyphenyl)glycine (o,p-EDDHA) is also known in the art. Contrary to o,o-EDDHA, in the o,p-EDDHA isomer one of the hydroxy groups is in the para-position of the benzene ring. For this reason, the ferric chelate of o,p-EDDHA shows a coordination number of 5 and its complexation affinity to iron is weaker than that of o,o-EDDHA. This compound has often being regarded as an undesired by-product being incurred by the manufacturing process of o,o-EDDHA.

Gómez-Gallego et al. (c.f. Chem. Eur. J. 2005, 11, 5997-6005) propose a model for explaining the reduction of the Fe(III)-o,o-EDDHA chelate by a ferric chelate reductase. According to it, the reduction of said chelate does not take place on the complex in the octahedral closed form, wherein the 6 chelating points of o,o-EDDHA are coordinated to the Fe(III), but on a hexacoordinate open species formed at the acid pH of the rhizosphere. As showed in Scheme 5 of said report, one of the hydroxy groups in the ortho-position would not be coordinated with the Fe(III), thus generating a vacant coordination site that would be filed with a water molecule. The complex Fe(III)-o,p-EDDHA, wherein one of the hydroxy groups is in the para-position, would already be in the required open form and could be reduced directly by the enzyme.

WO2005/095305 discloses isomeric mixtures comprising both (o,o-EDDHA) and (o,p-EDDHA), wherein the molar ratio of (o,p-EDDHA) to (o,o-EDDHA) is higher than 0.8:1, as nutrients for agricultural crop plants and agents for treatment of chlorosis in such plants.

SUMMARY OF THE INVENTION

The properties of the commercially available chelating agents currently used for the treatment of iron deficiency related plant diseases (e.g. iron chlorosis), such as those based in EDDHA and known derivatives thereof, are still not completely satisfactory. For instance, it has been observed that current chlorosis treatments based on o,o-EDDHA show a delayed effect in plants. WO2005/095305 proposes to solve this problem by employing isomeric mixtures of o,o-EDDHA and o,p-EDDHA, as said above. However, o,p-EDDHA/$Fe^{3+}$ shows lower stability than o,o-EDDHA/$Fe^{3+}$. (Yunta et al. *Journal of Agricultural and Food Chemistry*, 2003, 51, 5391-5399) so it is quite reactive in soils.

Properties that are desirable in a compound useful for the treatment of iron chlorosis are described in Lucena, J. J. Iron *Fertilizers in Correcting Iron Deficiencies in Plants*. Chapter 5, In Iron Nutrition in Plants and Rhizospheric Microorganism 2006, pp 103-127, Springer-Verlag Academic Publishers.

The problem to be solved by the present invention is to provide alternative products that may be useful for the treatment of iron deficiency related plant diseases. These products may have improved properties regarding the currently known treatments.

The solution is based on the fact that the present inventors have identified that by eliminating one of the carboxylic groups of EDDHA and maintaining or modulating the hydroxyphenyl groups, the chelating affinity for polyvalent metals, particularly for iron, is retained, while some other properties may be improved, particularly those that make them useful for the treatment of iron chlorosis. See working examples 1-7 herein for a further description.

Accordingly, a first aspect of the invention relates to a compound of formula (I):

wherein
$X^1$ is a $C_6$ or a $C_{10}$ aromatic system having a hydroxy group in the alpha position, being optionally substituted by up to four substituents independently selected from the group consisting of: phospho, sulfo, halo, carboxy, acetoxy, $C_1$-$C_4$ alkoxy or linear or branched $C_1$-$C_4$ alkyl.
$X^2$ is a $C_6$ or a $C_{10}$ aromatic system having a hydroxy group in the alpha position, or a five or six membered heterocycle having in the alpha position a heteroatom selected from the group consisting of N, O and S, optionally comprising other N, O or S atoms in their structure, and having from 0-3 double bonds, said aromatic, or heterocyclic system being optionally substituted by up to four substituents independently selected from the group consisting of: phospho, sulfo, halo, carboxy, acetoxy, $C_1$-$C_4$ alkoxy, linear or branched $C_1$-$C_4$ alkyl.

Y is $(CH_2)_n$ or is a xylylene group of formula:

n is an integer selected from 2, 3 and 4, $R^1$, $R^2$ are independently selected from the group consisting of H, linear or branched $C_1$-$C_4$ alkyl, $C_6$ or $C_{10}$ aryl.

In a second aspect the invention relates to a process for preparing a compound of formula (I) as defined in the first aspect of the invention and in its corresponding embodiments, which process comprises the step of reducing a compound of formula (II):

wherein $X^1$, $X^2$ and Y are as defined above, in an appropriate solvent system, in the presence of a reducing agent.

In a third aspect the invention relates to the use of a compound of formula (I), as defined in the first aspect of the invention and its corresponding embodiments, as a complex forming agent for polyvalent metals.

In a fourth aspect the invention relates to a chelate of a compound of the formula (I), as defined in the first aspect of the invention and its corresponding embodiments, with one or more polyvalent metals.

In a fifth aspect the invention relates to an agrochemical composition comprising a compound of formula (I), as defined in the first aspect of the invention and its corresponding embodiments, or a polyvalent metal chelate thereof.

In a sixth aspect the invention relates to the use of a compound, as defined in the first aspect of the invention and its corresponding embodiments, or a polyvalent metal chelate thereof, for the preparation of a composition for treating an iron deficiency related plant disease.

In a seventh aspect the invention relates to an intermediate of formula (II):

wherein $X^1$, $X^2$ and Y are as defined above, in solid form.

In a eighth aspect the invention relates to the use of the intermediate of formula (II) as defined in the seventh aspect of the invention and its corresponding embodiments, for the preparation of a compound of formula (I), as defined in the first aspect of the invention and its corresponding embodiments.

Without wishing to be bound by theory, as reported in Chem. Eur. J. 2005, 11, 5997, the effectiveness of Fe(III)-o, o-EDDHA to relief iron chlorosis requires the generation of a vacant coordination site. This fact explains the high efficiency of o,p-EDDHA a compound in which one of the phenolic groups is unable to coordinate the metal. Advantageously the new compounds described in the invention have only five groups able to coordinate with the metal. This point should be essential for their activity.

Furthermore, most of the derivatives of EDDHA known in the art and employed for the treatment of iron deficiency related plant diseases are symmetrical compounds, except for the o,p-EDDHA, which is an isomer of EDDHA. On the contrary, all the compounds of formula (I) are non-symmetrical compounds, since they lack one of the two carboxylic groups of EDDHA. Therefore, the known methods for the preparation of EDDHA derivatives were not directly applicable to the compounds of the invention. This has forced the inventors to develop a new method of synthesis for preparing the said compounds of formula (I).

Throughout the description and claims the word "comprise" and variations of the word, such as "comprising", is not intended to exclude other technical features, additives, components, or steps. The content of the application from which priority is claimed, as well as the contents of the abstracts of the priority application and the present application, are incorporated herein as reference.

Additional objects, advantages and features of the invention will become apparent to those skilled in the art upon examination of the description or may be learned by practice of the invention. The following examples are provided by way of illustration, and it is not intended to be limiting of the present invention.

DEFINITIONS

By linear or branched $C_1$-$C_4$ alkyl, is taken to mean herein a linear or branched alkyl group which contains up to 4 atoms of carbon. Thus it includes, for example, methyl, ethyl, propyl, isopropyl, butyl, isobutyl, sec-butyl and tert-butyl.

By $C_1$-$C_4$ alkoxy it is meant herein the alkyl groups mentioned above bound through oxygen, examples of which include methoxy, ethoxy, isopropoxy, tert-butoxy, and the like.

The term halo, in this invention, refers to F, Cl, Br, I, preferably Cl.

A $C_6$ or a $C_{10}$ aromatic system or a $C_6$ or a $C_{10}$ aryl group include phenyl and naphtyl.

DETAILED DESCRIPTION OF PARTICULAR EMBODIMENTS

As defined above, $X^2$ in the compounds of formula (I) is a $C_6$ or a $C_{10}$ aromatic system having a hydroxy group in the alpha position, or a five or six membered heterocycle having in the alpha position a heteroatom selected from the group consisting of N, O and S, optionally comprising other N, O or S atoms in their structure, and having from 0-3 double bonds, said aromatic, or heterocyclic system being optionally substituted by up to four substituents independently selected from the group consisting of: phospho, sulfo, halo, carboxy, acetoxy, $C_1$-$C_4$ alkoxy, linear or branched $C_1$-$C_4$ alkyl. Heterocycle as meant herein includes both non-aromatic heterocycles (e.g. 2-azetidinyl, 2-pyrrolidyl, 2-piperidinyl), and heteroaromatic rings. Preferably said heterocycle is heteroaromatic.

Preferred compounds of formula (I) are those wherein $X^2$ is selected from the group consisting of 2-hydroxyphenyl, 2-hydroxy-naphthyl, 2-furyl, 2-thienyl, 2-pyrrolyl, 2-pyridyl, 4-pyridimidinyl, 2-pyrazinyl optionally substituted by 2 or 1 substituents independently selected from the group consisting of: phospho, sulfo, halogen, $C_1$-$C_4$ alkoxy, carboxy, acetoxy, linear or branched $C_1$-$C_4$ alkyl. Preferred optional substituents include methyl, phenyl, phospho, sulfo, carboxy, acetyl.

More preferred compounds of formula (I) are those wherein $X^1$ is 2-hydroxyphenyl or 2-hydroxynaphthyl, optionally substituted by 2 or 1 substituents independently selected from the group consisting of methyl or methoxy. Yet more preferred are those wherein $X^1$ is 2-hydroxyphenyl.

In the compounds of formula (I), preferably Y is $(CH_2)_n$, and more preferably n is 2. When Y is a xylylene group as defined above, preferably both $R^1$ and $R^2$ are H.

In a preferred embodiment, compounds of formula (I) are those wherein Y is $(CH_2)_n$, and more preferably n is 2, $X^1$ is 2-hydroxyphenyl, $X^2$ is selected from the group consisting of 2-hydroxyphenyl, 2-hydroxynaphthyl, 2-furyl, 2-thienyl, 2-pyrrolyl, 2-pyridyl, 4-pyrimidinyl, 2-pyrazinyl, optionally substituted by 2 or 1 substituents independently selected from the group consisting of: $C_1$-$C_4$ alkyl, $C_1$-$C_4$ alkoxy, carboxy, sulfo, acetoxy.

The most particularly preferred compounds are selected from the group consisting of:
2-(2-((2-hydroxybenzyl)amino)ethylamino)-2-(2-hydroxyphenyl)acetic acid,
2-(2-((2-hydroxy-1-naphtyl)methylamino)ethylamino)-2-(2-hydroxyphenyl)acetic acid,
2-(2-((pyridin-2-yl)methylamino)ethylamino)-2-(2-hydroxyphenyl)acetic acid,
2-(2-((1H-pyrrol-2-yl)methylamino)ethylamino)-2-(2-hydroxyphenyl)acetic acid.

Preferred methods include, but are not limited to, those described below. The reactions are carried out in the solvents appropriate for the reagents and materials used and suited for the transformations carried out. An expert in organic synthesis will understand that the functional groups present in the molecule must be consistent with the proposed transformations. This may in some cases require modifying the order of the synthesis steps or selecting one particular method rather than another, in order to obtain the desired compound of the invention. Moreover, in some of the procedures described below it may be desirable or necessary to protect the reagent functional groups present in the compounds or intermediates of this invention with conventional protecting groups. Various protecting groups and procedures for introducing them and removing them are described in Greene and Wuts (*Protective Groups in Organic Synthesis*, Wiley and Sons, 1999). All the references cited herein are incorporated integrally by reference.

The compounds of formula (I) as defined above, can be prepared by a process which comprises the step of reducing a compound of formula (II):

wherein $X^1$, $X^2$ and Y are as defined above, in an appropriate solvent system, in the presence of a reducing agent.

The reaction may be carried out in different solvent systems. Suitable solvent systems include $C_1$-$C_4$ alcohols such as methanol and ethanol, acetic acid, water and mixtures thereof. Preferably the reaction is carried out in methanol.

Suitable reducing agents are hydrides and hydrogen with a metal catalyst. Preferably, the reducing agent is selected from the group consisting of borohydrides, such as sodium cyanoborohydride, sodium triacetoxyborohydride, sodium borohydride. Better results are obtained when the reducing agent used is sodium borohydride or Pd hydrogenation.

The reaction is preferably carried out at temperature ranging from 15° C. to 40° C. Better results are obtained when carried out from 18° C. to 25° C.

In a preferred embodiment, the process for preparing a compound of formula (I) according to the second aspect of the invention, further previously comprises the step of preparing said compound of formula (II) by reacting a compound of formula (III) with a compound of formula (IV):

wherein $X^1$, $X^2$ and Y are as defined above, in an appropriate solvent system.

The reaction between a compound of formula (III) with a compound of formula (IV) may be carried out in different solvent systems. Suitable solvent systems include $C_1$-$C_4$ alcohols such as methanol and ethanol; water; nitriles such as acetonitrile; ketones such as 2-butanone; and mixtures thereof. Preferably the reaction is carried out in methanol, ethanol, water or mixtures thereof.

In a preferred embodiment, the reaction between a compound of formula (III) with a compound of formula (IV), and the subsequent reduction of the compound of formula (II) obtained to prepare a compound of formula (I) is carried out as a one pot reaction.

The best conditions to carry out the process vary according to the parameters considered by the person skilled in the art, such as the starting materials, temperature and similar. Such reaction conditions may be easily determined by the person skilled in the art by routine tests, and with the teaching of the examples included in this document.

Compounds of formula (III) are described in the literature and/or can be prepared by methods analogous to those known in the state of the art (e.g. in U.S. Pat. No. 5,679,704, DE3329028 A1 and WO-2006045852 A1) from products commercially available.

A compound of formula (I) as defined above may be used as a complex forming agent for polyvalent metals. Preferably, said polyvalent metal is at least one polyvalent metal selected from the group consisting of iron, nickel, zinc, manganese, ytterbium, gadolinium, cobalt and copper. More preferably, said metal is iron.

A compound of the formula (I) as defined above may form chelates with one or more polyvalent metals. Preferably, said polyvalent metal is at least one polyvalent metal selected from the group consisting of iron, nickel, zinc, manganese, ytterbium, gadolinium, cobalt, copper, palladium, platinum and, gold. More preferably, said metal is iron. Such iron chelates may further contain e.g. an alkali- or alkaline earth metal, like sodium, potassium, calcium or magnesium, particularly sodium.

Chelates according to the invention may be used as active component in agriculturally acceptable compositions, as sole active component or in combination with other agriculturally active components, such as plant nutrients or plant fertilizers. Thus, agrochemical compositions according to the invention comprise a compound of formula (I) as defined above, or a metal chelate thereof. Said compositions may further comprise agriculturally acceptable carriers. The composition is preferably applied in the form of a solution or suspension by injecting into the soil.

The other agriculturally acceptable active ingredients may be additional fertilizers, micronutrient donors or other preparations that influence plant growth and development or plant protection products like selective herbicides or insecticides, fungicides, bactericides, nematicides, molluscicides, or mixtures of several of such preparations, if desired.

Agriculturally acceptable active ingredients also include other chelating agents. Said chelating agents include ethylene diamine tetracetic acid (EDTA), diethylene triamine pentacetic acid (DTPA), o,o-EDDHA and o,p-EDDHA. In one embodiment, the agrochemical compositions of the invention also comprise o,o-EDDHA.

Agriculturally acceptable carriers may be natural or regenerated mineral substances, solvents, dispersants, wetting agents, tackifiers, thickeners or binders. Such carriers and additives are described, for example, in WO 95/30651.

The compounds of formula (I) according to the invention are useful for treating an iron deficiency related plant disease. Preferably, said disease is iron chlorosis.

Preferred intermediates of formula (II) are those wherein $X^1$ is 2-hydroxyphenyl.

EXAMPLES

Example 1

2-(2-((2-hydroxybenzyl)amino)ethylamino)-2-(2-hydroxyphenyl)acetic acid

Step 1. Intermediate of formula (II)
($X^1$=2-hydroxyphenyl, Y=(CH$_2$)$_2$,
$X^2$=2-hydroxybenzyl)

To a solution of the 2-(2-aminoethylamino)-2-(2-hydroxyphenyl)acetic acid hydrochloride in water at pH 7.3, was added an equimolar amount of salicylaldehyde in ethanol. After stirring for 1 h at room temperature, the title Schiff base was filtered and obtained as a solid in 80% yield.

$^1$H-NMR (300 MHz, DMSO-d6, 2.5, ppm): δ=8.54 (s, 1H, CH=N), 7.48 (d, 1H, J=7.5 Hz, Ar), 7.34 (t, 1H, J=7.62 Hz, Ar), 7.30 (d, 1H, J=7.32 Hz, Ar), 7.18 (m, 1H, Ar), 6.92-6.70 (m, 4H, Ar), 4.62 (s, 1H, CH), 3.83 (m, 4H, CH$_2$), 3.15 (m, 1H, CH$_2$), 3.02 (m, 1H, CH$_2$).

Step 2. 2-(2-((2-hydroxybenzyl)amino)ethylamino)-2-(2-hydroxyphenyl)acetic acid

The hydrogenation of the of the Schiff base obtained in Step 1 in MeOH (10% Pd/C) at room temperature yielded the title product as brown solid (80%).

$^1$H-NMR (500 MHz, D$_2$O, 4.8 (HDO), ppm): δ=7.20-7 (m, 4H, Ar), 6.79-6.66 (m, 4H, Ar), 4.36 (s, CH), 3.87 (s, 2H, CH$_2$), 2.84-2.69 (m, 4H, CH$_2$).

Example 2

2-(2-((2-hydroxy-1-naphtyl)methylamino)ethylamino)-2-(2-hydroxyphenyl)acetic acid Step 1. Intermediate of formula (II)
($X^1$=2-hydroxyphenyl, Y=(CH$_2$)$_2$,
$X^2$=2-hydroxy-1-naphtyl)

Following Example 1, but starting from equimolar amounts of 2-(2-aminoethylamino)-2-(2-hydroxyphenyl)acetic acid hydrochloride and 1-formyl-β-naphthol the Schiff base of the title was obtained as yellow solid in 70% yield.

$^1$H-NMR (300 MHz, DMSO, 2.5, ppm): δ=9.11 (s, 1H, CH—N), 8.055 (d, 1H, J=8.35 Hz, Ar), 7.72 (d, 1H, J=9.44 Hz, Ar), 7.63 (d, 1H, J=7.10 Hz, Ar), 7.42 (d, 2H, J=7.07 Hz, Ar), 7.25 (d, 1H, J=9.44 Hz, Ar), 7.17 (d, 2H, J=7.11 Hz, Ar), 6.75-6.67 (m, 2H, Ar), 4.43 (s, 1H), 3.86-3.78 (m, 2H, CH$_2$), 3.2-3.02 (m, 1H CH$_2$), 2.92-2.8 (m, 1H, CH$_2$).

Step 2. 2-(2-((2-hydroxy-1-naphtyl)methylamino)ethylamino)-2-(2-hydroxyphenyl)acetic acid A mixture of equimolar amounts of the Schiff base obtained in Step 1, NaBH$_3$CN and a catalytic amount of Zn$_2$Cl in MeOH was stirred at room temperature for 3 h. The solvent was removed by evaporation and the title product was obtained as brown solid (85% yield).

$^1$H-NMR (500 MHz, D$_2$O, 4.8 (HDO), ppm): δ=7.7-7.55 (m, 3H, Ar), 7.45-7.37 (m, 1H, Ar), 7.3-7.15 (m, 2H, Ar), 7.06 (d, 1H, J=5.67 Hz, Ar), 6.95 (d, 1H, J=9.17 Hz, Ar), 6.8-7.2 (m, 2H, Ar), 5.02 (s, 1H), 4.23 (s, 2H), 3.22-3.073 (m, 4H).

Example 3

2-(2-((pyridin-2-yl)methylamino)ethylamino)-2-(2-hydroxyphenyl)acetic acid

Step 1. Intermediate of formula (II)
($X^1$=2-hydroxyphenyl, Y=(CH$_2$)$_2$, $X^2$=pyridin-2-yl)

The procedure of Example 1 is followed, but starting from equimolar amounts of 2-(2-aminoethylamino)-2-(2-hydroxyphenyl)acetic acid hydrochloride and 2-pyridinecarboxaldehyde at pH 7. After 20 h at room temperature the solvent was removed and the title Schiff base was obtained as yellow solid in 90% yield.

$^1$H-NMR (300 MHz, DMSO, 2.5, ppm): δ=8.63 (bs, 1H, J=4.77 Hz, CH=N), 8.5-8.1 (m, 1H, Ar), 8.0-7.84 (m, 2H, Ar), 7.46 (t, 1H, Ar J=6.58 Hz,), 7.21-7.1 (m, 1H, Ar), 7.05-6.95 (m, 1H, Ar), 6.88-6.73 (m, 2H, Ar), 4.59 (s, 1H, CH), 3.9 (m, 2H, CH$_2$), 3.1-3.0 (m, 2H, CH$_2$).

Step 2. 2-(2-((pyridin-2-yl)methylamino)ethylamino)-2-(2-hydroxyphenyl)acetic acid A mixture of equimolar amounts of the Schiff base obtained in Step 1 and NaBH$_4$ in MeOH was stirred at room temperature for 20 h. The solvent was removed by evaporation and the title product was obtained as white solid (95% yield).

$^1$H-NMR (300 MHz, D$_2$O, 4.8 (HDO) ppm): δ=8.4-8.36 (m, 1H, Ar), 7.82 (td, 1H, J$_1$=7.65 Hz, J$_2$=1.38 Hz, Ar), 7.77-7.72 (m, 2H, Ar), 7.36-7.25 (m, 2H, Ar), 7.2-7.0 (m, 1H, Ar), 6.74-6.65 (m, 1H, Ar), 4.38 (s, CH), 3.76 (s, 2H, CH$_2$), 2.78-2.6 (m, 4H, CH$_2$).

Example 4

2-(2-((1H-pyrrol-2-yl)methylamino)ethylamino)-2-(2-hydroxyphenyl)acetic acid

Step 1. Intermediate of formula (II)
(X$^1$=2-hydroxyphenyl, Y=(CH$_2$)$_2$,
X$^2$=1H-pyrrol-2-yl)

Following the procedure of Example 1, but starting from equimolar amounts of 2-(2-aminoethylamino)-2-(2-hydroxyphenyl)acetic acid hydrochloride and pyrrole-2-carboxaldehyde, the title Schiff base was obtained after stirring at room temperature for 20 h as orange solid in 90% yield.

$^1$H-NMR (300 MHz, DMSO, 2.5, ppm): δ=8.09 (s, 1H, CH=N), 7.35-7.20 (m, 1H, Ar), 7.0-6.95 (m, 1H, Ar), 6.87 (s, 1H, Ar), 6.75-6.65 (m, 1H, Ar), 6.5-6.4 (m, 1H, Ar), 6.3-6.2 (m, 1H, Ar), 6.115-6.05 (m, 1H, Ar), 4.11 (s, 1H, CH), 3.65-3.5 (m, 2H, CH$_2$), 2.9-2.6 (m, 2H, CH$_2$).

Step 2. 2-(2-((1H-pyrrol-2-yl)methylamino)ethylamino)-2-(2-hydroxyphenyl)acetic acid A mixture of equimolar amounts of the Schiff base obtained in Step 1 and NaBH$_4$ in MeOH was stirred at room temperature for 20 h. The solvent was removed by evaporation and the title product was obtained as orange solid (94% yield).

$^1$H-NMR (500 MHz, D$_2$O, 4.8 (HDO), ppm): δ=7.2-7.1. (m, 2H, Ar), 6.80-6.69 (m, 3H, Ar), 6.15-6.25 (m, 2H, Ar), 4.44 (s, 1H), 3.70 (s, 2H, CH$_2$), 2.85-2.6 (m, 4H, CH$_2$).

Example 5

2-(2-((imidazol-4(5)-yl)methylamino)ethylamino)-2-(2-hydroxyphenyl)acetic acid

Step 1. Intermediate of formula (II) (X$^1$=2-hydroxyphenyl, Y=(CH$_2$)$_2$, X$^2$=imidazol-4(5)-yl)

To a solution of the 2-(2-aminoethylamino)-2-(2-hydroxyphenyl)acetic acid hydrochloride in water at pH 7.2, was added an equimolar amount of 4(5)-formylimidazole in methanol. After stirring for 24 h at room temperature, the title Schiff base was filtered and obtained as a solid in quantitative yield.

$^1$H-NMR (300 MHz, CD$_3$OD, 3.31 ppm): δ=8.21 (broad s, 1H, CH=N), 7.76 (s, 1H, CH=N), 7.49 (s, 1H, CH=N), 7.23 (dt, 1H, J$_1$=7.56 Hz, J$_2$=1.35 Hz, Ar), 7.10 (td, 1H, J$_1$=1.38 Hz, J$_2$=7.56 Hz, Ar), 6.77 (m, 2H, Ar), 5.74 (1H, NH), 4.44 (s, 1H, CH), 3.72-3.70 (m, 2H, CH$_2$), 3.08-3.0 (m, 1H, CH$_2$), 2.95-2.34 (m, 1H, CH$_2$).

Step 2. 2-(2-((imidazol-4(5)-yl)methylamino)ethylamino)-2-(2-hydroxyphenyl)acetic acid The hydrogenation of the Schiff base obtained in Step 1 in MeOH (10% Pd/C) at room temperature yielded the title product as a solid (35%).

$^1$H-NMR (500 MHz, D$_2$O, 4.8 (HDO) ppm): δ=7.55 (s, 1H, C=N), 7.06-7.0.3 (m, 2H, Ar), 6.88 (s, 1H, C=N), 6.68-6.64 (m, 2H, Ar), 4.33 (s, 1H, CH), 3.59 (s, 2H, CH$_2$), 2.76-2.56 (m, 4H, CH$_2$).

Example 6

2-(2-((1H-imidazol-2-yl)methylamino)ethylamino)-2-(2-hydroxyphenyl)acetic acid

Step 1. Intermediate of formula (II)
(X$^1$=2-hydroxyphenyl, Y=(CH$_2$)$_2$,
X$^2$=1H-imidazol-2-yl)

To a solution of the 2-(2-aminoethylamino)-2-(2-hydroxyphenyl)acetic acid hydrochloride in water at pH 7.2, was added an equimolar amount of 2-formylimidazole in methanol. After stirring for 24 h at room temperature, the title Schiff base was filtered and obtained as a solid in quantitative yield.

$^1$H-RMN (500 MHz, CD$_3$OD, 3.31 ppm) δ=8.24 (broad s, 1H, CH=N), 7.18 (s, 2H, CH=N), 7.10-6.97 (m, 2H, Ar), 6.79-6.73 (m, 2H, Ar), 5.72 (broad s, 1H, NH), 4.36 (s, 1H, CH), 3.79-3.75 (m, 2H, CH$_2$), 3.03-2.94 (m, 1H, CH$_2$), 2.89-2.84 (m, 1H, CH$_2$).

Step 2. 2-(2-((1H-imidazol-2-yl)methylamino)ethylamino)-2-(2-hydroxyphenyl)acetic acid The hydrogenation of the of the Schiff base obtained in Step 1 in MeOH (10% Pd/C) at room temperature yielded the title product as a solid (34%).

$^1$H-RMN (500 MHz, D$_2$O, 4.8 (HDO) ppm) δ=7.55 (s, 1H, C=N), 7.06-7.03 (m, 2H, Ar), 6.88 (s, 1H, C=N), 6.68-6.64 (m, 2H, Ar), 4.33 (s, 1H, CH), 3.59 (s, 2H, CH$_2$), 2.76-2.56 (m, 4H, CH$_2$).

Example 7

2-(2-((piperidin-2-yl)methylamino)ethylamino)-2-(2-hydroxyphenyl)acetic acid

Step 1. Intermediate of formula (II)
(X$^1$=2-hydroxyphenyl, Y=(CH$_2$)$_2$,
X$^2$=piperidin-2-yl)

To a solution of the 2-(2-aminoethylamino)-2-(2-hydroxyphenyl)acetic acid hydrochloride in water at pH 7.2, was added an equimolar amount of 2-formyl-N-terbutoxycarbonyl-piperidine in methanol. After stirring for 24 h at room temperature, the title Schiff base was filtered and obtained as a solid in quantitative yield.

$^1$H-NMR (300 MHz, DMSO-d6, 2.5, ppm): δ=7.57 (s, 1H, C=N), 7.28-7.26 (m, 2H, Ar), 7.0-6.96 (m, 2H, Ar), 4.5 (s, 1H, CH), 4.14-4.05 (m, 1H, CH), 3.3-2.80 (m, 6H, CH$_2$), 1.49-1.36 (m, 6H, CH$_2$), 1.36 (s, 9H, CH$_3$).

Step 2. 2-(2-((piperidin-2-yl)methylamino)ethylamino)-2-(2-hydroxyphenyl)acetic acid The hydrogenation of the of the Schiff base obtained in Step 1 in MeOH (10% Pd/C) at room temperature, followed by removal of the terbutoxycarbonyl (BOC) group with 1 mL of 10% H$_2$SO$_4$ in 10 mL dioxane, 24 h at room temperature, yielded the title product as a solid (60%).

$^1$H-RMN (500 MHz, D$_2$O, 4.8 (HDO) ppm): δ=7.21-7.16 (m, 2H, Ar), 6.72-6.67 (m, 2H, Ar), 4.35 (s, 1H, CH), 3.56-

3.51 (m, 1H, CH), 3.1-2.52 (m, 8H, $CH_2$), 1.49-1.45 (m, 2H, $CH_2$), 1.13-1.03 (m, 4H, $CH_2$).

Example 8

2-(2-((pyrrolidin-2-yl)methylamino)ethylamino)-2-(2-hydroxyphenyl)acetic acid

Step 1. Intermediate of formula (II)
($X^1$=2-hydroxyphenyl, Y=$(CH_2)_2$, $X^2$=pyrrolidin-2-yl)

To a solution of the 2-(2-aminoethylamino)-2-(2-hydroxyphenyl)acetic acid hydrochloride in water at pH 7.2, was added an equimolar amount of 2-formyl-N-terbutoxycarbonyl-pyrrolidine in methanol. After stirring for 24 h at room temperature, the title Schiff base was filtered and obtained as a solid in quantitative yield.

$^1$H-RMN (500 MHz, DMSO-d6, 2.5, ppm): δ=7.57 (broad s, 1H, C=N), 7.27 (d, 1H, J=7.35 Hz, Ar), 7.01-6.91 (m, 1H, Ar), 6.66-6.59 (m, 2H, Ar), 4.6 (m, 1H, CH), 3.92 (s, 1H, CH), 2.71-2.6 (m, 1H, $CH_2$), 2.59-2.45 (m, 1H, $CH_2$), 1.99-1.75 (m, 4H, $CH_2$), 1.38-1.37 (m, 2H, $CH_2$), 1.37 (s, 9H, $CH_3$).

Step 2. 2-(2-((pyrrolidin-2-yl)methylamino)ethylamino)-2-(2-hydroxyphenyl)acetic acid The hydrogenation of the of the Schiff base obtained in Step 1 in MeOH (10% Pd/C) at room temperature, followed by removal of the BOC group with 1 mL of 10% $H_2SO_4$ in 10 mL dioxane, 24 h at room temperature, yielded the title product as a solid (50%).

$^1$H-RMN (500 MHz, $D_2O$, 4.8 (HDO) ppm): δ=7.31-7.26 (m, 2H, Ar), 6.91-6.87 (m, 2H, Ar), 5.1 (s, 1H, CH), 3.9-3.83 (m, 1H, CH), 3.44-3.20 (m, 8H, $CH_2$), 1.96-1.65 (m, 4H, $CH_2$).

Example 9

2-(2-((2-hydroxybenzyl)amino)ethylamino)-2-(2-hydroxy-4-methylphenyl)acetic acid Step 1. Intermediate of formula (II)
($X^1$=2-hydroxy-4-methylphenyl, Y=$(CH_2)_2$, $X^2$=2-hydroxybenzyl)

To a solution of the 2-(2-aminoethylamino)-2-(2-hydroxy-4-methylphenyl)acetic acid hydrochloride in water at pH 7.2, was added an equimolar amount of salicylaldehyde in ethanol. After stirring for 1 h at room temperature, the title Schiff base was filtered and obtained as yellow solid in 65% yield.

$^1$H-NMR (300 MHz, DMSO-d6, 2.5, ppm): δ=8.54 (s, 1H, CH=N), 7.45 (d, 1H, J=7.78 Hz, Ar), 7.33 (td, 1H, $J_1$=1.63 Hz, $J_2$=8.2 Hz, Ar), 7.08 (d, 1H, J=7.7 Hz, Ar), 6.9 (t, 2H J=7.27 Hz Ar), 6.61-6.58 (m, 2H, Ar), 4.56 (s, 1H, CH), 3.85-3.81 (m, 2H, $CH_2$), 3.17-3.09 (m, 1H, $CH_2$), 3.09-2.95 (m, 1H, $CH_2$), 2.18 (s, 3H, $CH_3$).

Step 2. 2-(2-((2-hydroxybenzyl)amino)ethylamino)-2-(2-hydroxy-4-methylphenyl)acetic acid The hydrogenation of the of the Schiff base obtained in Step 1 in MeOH (10% Pd/C) at room temperature yielded the title product as brown solid (75%).

$^1$H-NMR (500 MHz, $D_2O$, 4.8 (HDO), ppm): δ=7.22-7.1 (m, 3H, Ar), 6.72-6.64 (m, 4H, Ar), 4.37 (s, 1H, CH), 3.92 (s, 2H, $CH_2$), 2.59-2.81 (m, 4H, $CH_2$), 2.23 (S, 3H, $CH_3$).

Example 10

2-(2-((2-hydroxybenzyl)amino)ethylamino)-2-(2-hydroxy-5-methylphenyl)acetic acid Step 1. Intermediate of formula (II)
($X^1$=2-hydroxy-5-methylphenyl, Y=$(CH_2)_2$, $X^2$=2-hydroxybenzyl)

To a solution of the 2-(2-aminoethylamino)-2-(2-hydroxy-5-methylphenyl)acetic acid hydrochloride in water at pH 7.2, was added an equimolar amount of salicylaldehyde in ethanol. After stirring for 1 h at room temperature, the title Schiff base was filtered and obtained as yellow solid in 52% yield.

$^1$H-NMR (300 MHz, DMSO-d6, 2.5, ppm): δ=8.55 (s, 1H, C=N), 7.45 (d, 1H, J=7.6 Hz, Ar), 7.32 (t, 1H, J=8.81 Hz, Ar), 7.02 (s, 1H, Ar), 6.90 (t, 3H, J=7.56 Hz, Ar), 6.68 (d, 1H, J=8.13, Ar), 4.52 (s, 1H, CH), 3.85-3.80 (m, 2H, $CH_2$), 3.2.-3.12 (m, 1H, $CH_2$), 3.01-2.94 (s, 1H, $CH_2$), 2.17 (s, 3H, $CH_3$), Step 2. 2-(2-((2-hydroxybenzyl)amino)ethylamino)-2-(2-hydroxy-5-methylphenyl)acetic acid The hydrogenation of the of the Schiff base obtained in Step 1 in MeOH (10% Pd/C) at room temperature yielded the title product as brown solid (70%).

$^1$H-NMR (500 MHz, $D_2O$, 4.8 (HDO), ppm): δ=7.18 (t, 1H, J=6.14 Hz, Ar), 7.2-7.15 (m, 2H, Ar), 6.92-6.89 (s, 1H, Ar), 6.89-6.68 (m, 3H, Ar), 5.15 (s, 1H, CH), 4.16 (s, 2H, $CH_2$), 3.36-3.19 (m, 4H, $CH_2$), 2.19 (s, 3H, $CH_3$).

Example 11

Preparation of Ferric Chelates

The general procedure used for preparing the ferric chelates of the invention is the following:

To a solution of the ligand of formula (I) in NaOH (1:3 ligand:NaOH molar ratio), is added a solution of the equimolar amount of $FeCl_3.6H_2O$ in water. During the addition, the pH of the solution should be maintained between 6.0-8.0 by addition of NaOH or HCl, and finally adjusted to 7. The final solution is filtered through 0.45 μm cellulose membranes before use.

Example 12

Determination of Titrimetric Purity of the Chelating Agent

Photometric Titration

Chelating agent solution was prepared by dissolving an amount of chelating agent in the necessary amount of NaOH solution. Then pH is adjusted to 6 by the addition of MES biological buffer [2-(N-morpholino) ethanesulfonic acid] and maintaining at this pH with NaOH solution during the titration. Ionic strength is fixed at 0.1 M with NaCl and upper atmosphere was $N_2$ free of $CO_2$ The test solution was placed in a thermostated jacketed reaction vessel (i.e. 100 ml or 150 ml capacity) with an airtight cap fitted with gas inlet and outlet tubes, the combined pH glass electrode, the photometric detector and two piston burettes, tip extending below the surface of the solution, and a magnetic stirrer. The photometric titration consisted of the addition of a Fe(III) standard solution, previously standardized by Atomic Absorption Spectroscopy, to the chelating agent until the absorbance at 480 nm presents no changes. End-point titration could be calculated for two linear segments' intersection and also using smoothed second derivative method.

Potentiometric Titration

The chelating agent purities could also be determined by potentiometric titrations with a $Cu^{2+}$ ion selective electrode in the same conditions as before. The chelating agent solution is titrated with Cu(II) solution using selective Cu(II) electrode and reference electrode, $Cu^{2+}$ free cation is measured with the selective electrode. The end-point of the potentiometric titrations could be determined by Gran equation method or using the first derivative method. Previously, the Cu(II) solution used as titrant solution is standardize with EDTA-$Na_2$ solution and the selective electrode slope is determined by titration of NaCl solution fixed at pH=6 with Cu(II) as titrant solution.

Example 13

Determination of Agrochemical Activity

Efficacy of Fe Chelates to Provide Fe to Soybean Plants in Hydroponics.

Soybean seeds (Glycine max L. cv. Stine 0480) were germinated at 30° C. and 60% RH on paper moistened with 1 M $CaSO_4$ in dark for 2 days. Afterwards, seedlings were placed in 10 L containers (50 seedlings per container) filled with a 1/5 diluted EDTA buffered nutrient solution (macronutrients (mM)—1.0 $Ca(NO_3)_2$, 0.9 $KNO_3$, 0.3 $MgSO_4$, 0.1 $KH_2PO_4$; cationic micronutrients (μM)—5.0 EDTA/$Fe^{3+}$, 2.5 $MnSO_4$, 1.0 $CuSO_4$, 10 $ZnSO_4$, 1.0 $CoSO_4$, 1.0 $NiCl_2$, 115.5 $Na_2$EDTA; anionic micronutrients (μM)-35 NaCl, 10 $H_3BO_3$, 0.05 $Na_2MoO_4$; 0.1 mM HEPES) for 6 days. On the 7th day, in order to induce Fe chlorosis, seedlings were transferred to 12 L polypropylene buckets containing aerated full strength EDTA buffered nutrient solution but without $Fe^{3+}$-chelate. Plants were grown under these conditions until clear symptoms of Fe deficiency were observed (7 days) and then plants were placed in 2 L pots (6 plants per pot) covered with black plastic to avoid light exposure. The effect of different Fe chelates and doses were compared as Fe sources. Chelates used in the treatments were o,o-EDDHA/$Fe^{3+}$, o,p-EDDHA/$Fe^{3+}$, EDTA/$Fe^{3+}$ and Example 1/$Fe^{3+}$. The last one is the Fe chelate of the compound of the example 1: 2-(2-(((2-hydroxybenzyl)amino)ethylamino)-2-(2-hydroxyphenyl)acetic acid (DCHA). Nutrient solution contained macronutrients and anionic micronutrients as for the seedling period and the following cationic micronutrients composition: (μM) 1.0 $MnSO_4$, 0.5 $CuSO_4$, 0.5 $ZnSO_4$, 0.1 $NiCl_2$ and 0.1 $CoSO_4$. Also, 1 g·$L^{-1}$ of $CaCO_3$ was added to the nutrient solution to buffer pH at 7.5 and to simulate conditions of a calcareous soil. Plants were grown for 21 days in this nutrient solution in a growth chamber provided with fluorescent and sodium vapour lamps with a 16 h/30° C. and 50% humidity day and 8 h/25° C. and 70% humidity night regime. Water was added every 2 days and the nutrient solution was renewed every 7 days. Treatments were replicated four times in a completely randomised design. Plants were harvested after 7, 14 and 21 days.

During the experiment, SPAD readings with a chlorophyll-meter (Minolta SPAD-502) were taken for all leaf stages (average of two or three readings per stage) every second day. Only values measured for the youngest fully open leaves (the $2^{nd}$ stage at the $2^{nd}$ day, the third at the $10^{th}$ day and the fourth at the $20^{th}$ day) are here presented (Table 1)

TABLE 1

Effects of Fe chelates treatments on the SPAD index measured.

| | SPAD Time after treatments (days) | | |
|---|---|---|---|
| Treatments | 2 (2nd stage) | 10 (3rd stage) | 20 (4th stage) |
| T0 Control (without Fe) | 5.0 d | 3.4 d | — |
| T1 5 μM Example 1/Fe3+ | 8.4 abc | 32.8 a | 34.8 a |
| T2 10 μM Example 1/Fe3+ | 8.8 ab | 35.7 a | 35.0 a |
| T3 5 μM o,o-EDDHA/Fe3+ | 6.2 cd | 26.7 b | 30.2 a |
| T4 10 μM o,o-EDDHA/Fe3+ | 9.1 ab | 31.6 ab | 32.4 a |
| T5 5 μM o,p-EDDHA/Fe3+ | 8.1 abc | 30.9 ab | 32.2 a |
| T6 10 μM o,p-EDDHA/Fe3+ | 10.4 a | 33.1 a | 32.9 a |
| T7 5 μM EDTA/Fe3+ | 6.8 bcd | 6.9 d | 11.4 c |
| T8 10 μM EDTA/Fe3+ | 8.1 abc | 16.6 c | 19.9 b |

Different letters in the columns denote significant differences ($\alpha = 0.05$) among treatments according to the Duncan Test The chlorophyll and the recovery of plants after the treatments application were estimated by the SPAD index. Table 1 shows the time course of this parameter. Two days after the treatment application, plants treated with 10 μM o,p-EDDHA/$Fe^{3+}$ showed the highest SPAD index values but it only showed significant differences with 5 μM o,o-EDDHA/$Fe^{3+}$, 5 μM EDTA/$Fe^{3+}$ and —Fe treatments. Ten days after, plants treated with 5 μM and 10 μM Example 1/$Fe^{3+}$ and 10 μM o,p-EDDHA/$Fe^{3+}$ had significantly regreened in relation to 5 μM o,o-EDDHA/$Fe^{3+}$, 5 μM and 10 μM EDTA/$Fe^{3+}$ and —Fe treatments. At the end of the experiment (20 days after the treatments application), regardless of the doses, plants treated with Example 1, o,o-EDDHA and o,p-EDDHA Fe chelates (T1, T2, T3, T4, T5 and T6) had completely regreened showing significant SPAD index values concerning 5 μM and 10 μM doses of EDTA/$Fe^{3+}$ and —Fe treatments.

Considering the low doses applied and the trend observed, we can conclude that the product obtained in Example 1 presents a fast action to correct iron chlorosis, similar to o,p-EDDHA, but higher than o,o-EDDHA.

Root and shoot were separated and washed using Tween 80 (Merck) and HCl solution and fresh and dry (after oven dry procedure) weights were determined. Samples were ground and after dry digestion in a muffle furnace (480° C.), ashes are dissolved in HCl. Fe, Mn, Cu and Zn were analysed by atomic absorption spectrometry.

In Table 2 the Fe content in the plants in each sampling time for the treatments with the lower Fe application is presented. It can be observed that the novel compound Example 1/$Fe^{3+}$ is able to provide significantly higher amounts of iron and faster in this experimental conditions than the other treatments, even more than o,p-EDDHA in the third sampling time. However, when a large doses of Fe is used (10 μM, table 3) differences are only significant respect the treatment with EDTA/$Fe^{3+}$. It can be concluded that Example 1/$Fe^{3+}$ can be used in lower concentration than other chelates to correct the iron chlorosis.

TABLE 2

Fe content (μg Fe per plant) in plants treated with the low doses of chelates

| | Fe content (μg Fe per plant) | | |
|---|---|---|---|
| | 1st sampling 7 days after treatment | 2nd sampling 14 days after treatment | 3rd sampling 21 days after treatment |
| Control (without Fe) | 20.3 c | 10.0 c | 11.2 c |
| 5 μM Example 1/Fe3+ | 57.4 a | 152 a | 268 a |
| 5 μM o,o-EDDHA/Fe3+ | 26.0 bc | 83.6 b | 202 b |

TABLE 2-continued

Fe content (μg Fe per plant) in plants treated with the low doses of chelates

| | Fe content (μg Fe per plant) | | |
|---|---|---|---|
| | 1st sampling 7 days after treatment | 2nd sampling 14 days after treatment | 3rd sampling 21 days after treatment |
| 5 μM o,p-EDDHA/$Fe^{3+}$ | 43.0 ab | 128 a | 223 b |
| 5 μM EDTA/$Fe^{3+}$ | 14.2 c | 19.6 c | 22.6 c |

Different letters in the columns denote significant differences (α = 0.05) among treatments according to the Duncan Test.

TABLE 3

Fe content (μg Fe per plant) in plants treated with the high doses of chelates

| | Fe content (μg Fe per plant) | | |
|---|---|---|---|
| | 1st sampling 7 days after treatment | 2nd sampling 14 days after treatment | 3rd sampling 21 days after treatment |
| Control (without Fe) | 20.3 b | 10.0 b | 11.2 b |
| 10 μM Example 1/$Fe^{3+}$ | 69.3 a | 136 a | 235 a |
| 10 μM o,o-EDDHA/$Fe^{3+}$ | 61.4 a | 129 a | 254 a |
| 10 μM o,p-EDDHA/$Fe^{3+}$ | 77.8 a | 129 a | 259 a |
| 10 μM EDTA/$Fe^{3+}$ | 27.7 b | 32.6 b | 47.6 b |

Different letters in the columns denote significant differences (α = 0,.05) among treatments according to the Duncan Test.

Efficacy of Fe Chelates to Provide Fe to Soybean Plants in Soil Conditions

Soybean seeds (Glycine max L. cv. Stine 0480) were germinated at 30° C. and 60% RH on paper moistened with 1 M $CaSO_4$ in dark for 2 days. Afterwards, seedlings were placed in 10 L containers (50 seedlings per container) filled with a 1/5 diluted EDTA buffered nutrient solution (macronutrients (mM)—1.0 $Ca(NO_3)_2$, 0.9 $KNO_3$, 0.3 $MgSO_4$, 0.1 $KH_2PO_4$; cationic micronutrients (μM)—5.0 EDTA/$Fe^{3+}$, 2.5 $MnSO_4$, 1.0 $CuSO_4$, 10 $ZnSO_4$, 1.0 $CoSO_4$, 1.0 $NiCl_2$, 115.5 $Na_2EDTA$; anionic micronutrients (μM)—35 NaCl, 10 $H_3BO_3$, 0.05 $Na_2MoO_4$; 0.1 mM HEPES) for 4 days. Then, in order to induce Fe chlorosis, nutrient solution without iron was used for two more days and then plants were transplanted in 1 L pots (3 plants per pot) containing 700 g of a calcareous soil (380 mg·$Kg^{-1}$ calcium carbonate, 89 g·$Kg^{-1}$ $CaCO_3$ active, pH 7.70) and 300 g of lime sand covered with black plastic to avoid light exposure. The effect of different Fe chelates were compared as Fe sources: o,o-EDDHA/$Fe^{3+}$, o,p-EDDHA/$Fe^{3+}$, EDTA/$Fe^{3+}$ and Example 1/$Fe^{3+}$. The last one is the Fe chelate of the compound of the example 1: 2-(2-((2-hydroxybenzyl)amino)ethylamino)-2-(2-hydroxyphenyl)acetic acid. Plants were grown for 21 days in this soil conditions in a growth chamber provided with fluorescent and sodium vapour lamps with a 16 h/30° C. and 50% humidity day and 8 h/25° C. and 70% humidity night regime. Treatments were replicated five times in a completely randomised design. Single plants were harvested after 2, 7 and 21 days.

During the experiment, SPAD readings with a chlorophyll-meter (Minolta SPAD-502) were taken for all leaf stages (average of two or three readings per stage) every second day. Values measured for the $2^{nd}$ stage at the $2^{nd}$ day, the third at the $12^{th}$ day and the fourth and fifth at the $22^{th}$ day) are here presented (Table 4).

TABLE 4

Effects of Fe chelates treatments on the SPAD index measured in the soil experiment

| | SPAD Time after treatments (days) | | | |
|---|---|---|---|---|
| Treatments | 2 (2nd stage) | 12 (3rd stage) | 22 (4th stage) | 22 (5th stage) |
| Control (—Fe) | 19.1 | 12.6 | 9.0 | — |
| o,o-EDDHA/$Fe^{3+}$ | 22.4 | 42.1 | 34.1 | 28.8 |
| o,p-EDDHA/$Fe^{3+}$ | 25.8 | 41.2 | 33.0 | 21.0 |
| Example 1/$Fe^{3+}$ | 23.9 | 41.0 | 34.1 | 26.6 |

Different letters in the columns denote significant differences (α = 0.05) among treatments according to the Duncan Test.

Figure 1:
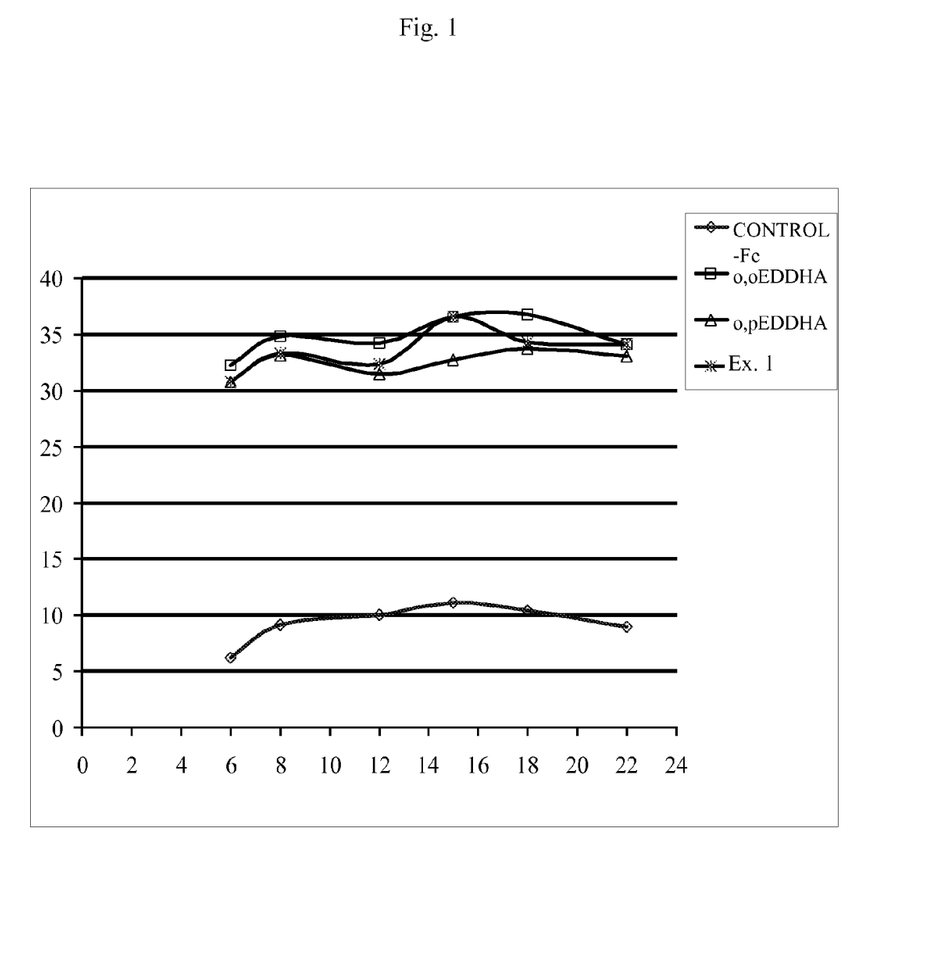
FIG. 1 shows the SPAD index of the fourth level, represented versus the days of treatment, for plants grown on soil treated with each of the tested compounds and the control.

All chelate treatments present higher SPAD indexes than control, as shown in FIG. 1. This and the visual symptoms indicate that the recovery from chlorosis using these chelates was complete. Two days after the treatment application, plants treated with o,p-EDDHA/$Fe^{3+}$ and Example 1/$Fe^{3+}$ presented the better recovery, due to the fast action of these compounds, and after that it is the treatment with the o,o-EDDHA/$Fe^{3+}$ the one which gives the highest values but similar to Example 1/$Fe^{3+}$.

In each sampling time shoots were separated and washed using Tween 80 (Merck) and HCl solution and fresh and dry (after oven dry procedure) weights were determined. Samples were ground and after dry digestion in a muffle furnace (480° C.), ashes were dissolved in HCl. Fe, Mn, Cu and Zn were analysed by atomic absorption spectrometry.

Figure 2:
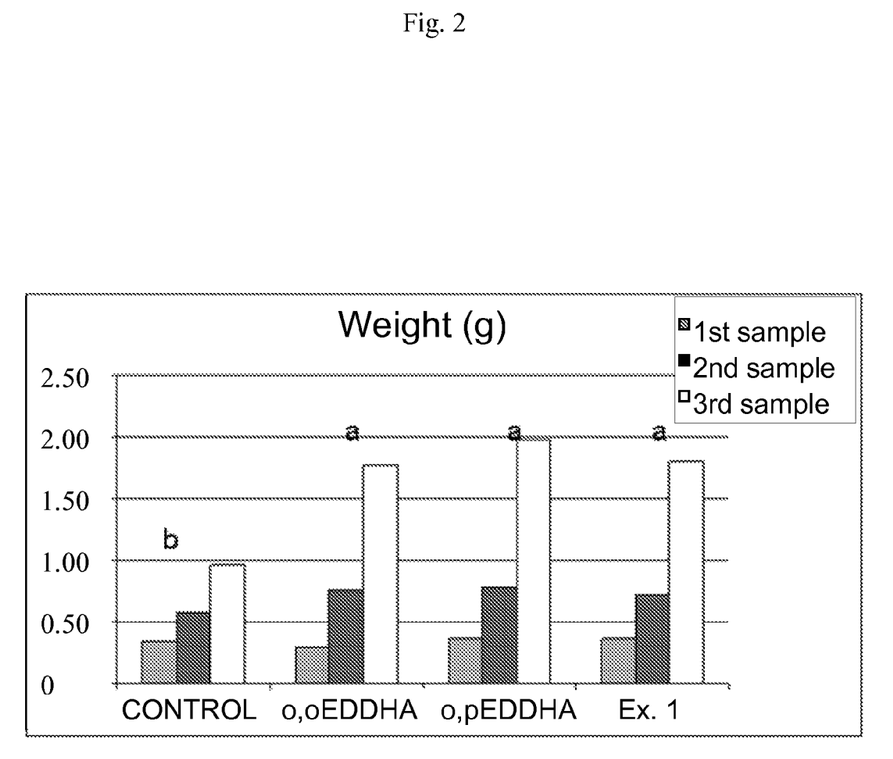
FIG. 2 shows the dry weight of shoots (expressed in grams) in the soil experiment, with the tested compounds and the control, at three sampling times.
Figure 3:
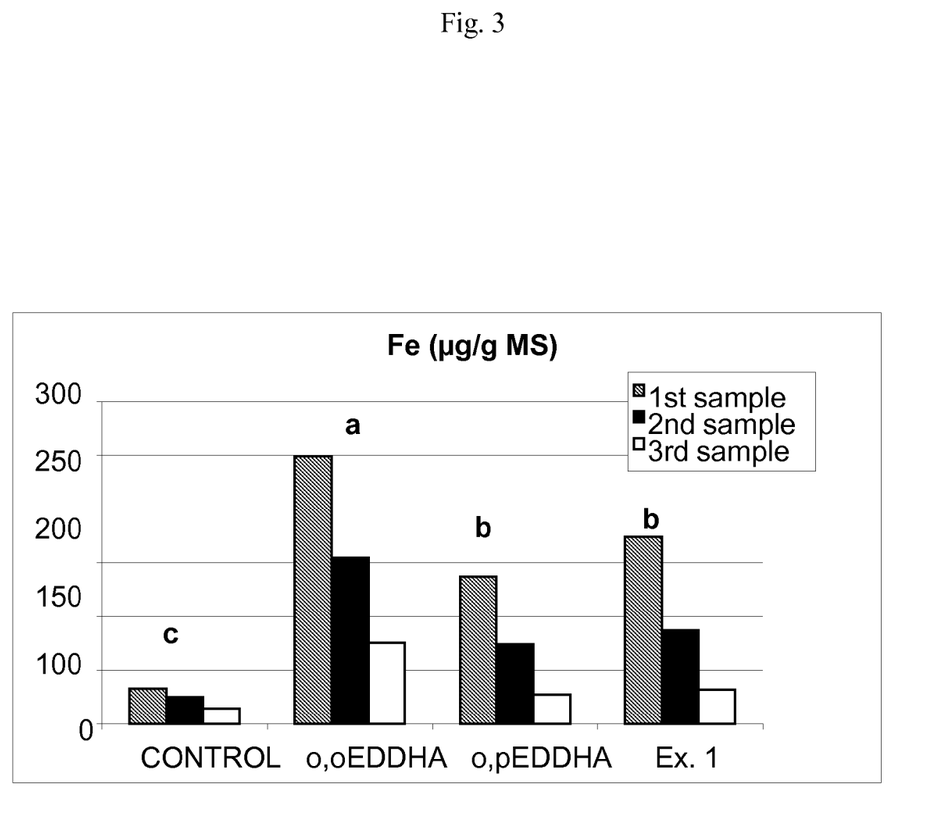
FIG. 3 shows the iron concentration in leaves of the plants treated with the tested compounds and the control, at three sampling times.

In FIG. 2 the dry weight obtained for the shoots is presented. Again the Example 1/$Fe^{3+}$ revealed as an efficient Fe chlorosis corrector. Also in FIG. 3 the iron concentration in leaves is shown for the three sampling times. The three iron chelates considerably increase the Fe concentration with respect to the control.

From this experiment, with only one treatment application, we can conclude that the product obtained in Example 1 is efficient to solve iron chlorosis in highly calcareous conditions. Its efficacy is related with its fast action mechanism.

The invention claimed is:
1. A compound of formula (I):

(I)

wherein
X$^1$ is a $C_6$ or a $C_{10}$ aromatic system having a hydroxy group in the alpha position, being optionally substituted by up to four substituents independently selected from the group consisting of: phospho, sulfo, halo, carboxy, acetoxy, $C_1$-$C_4$ alkoxy, linear and branched $C_1$-$C_4$ alkyl;
X$^2$ is a $C_6$ or a $C_{10}$ aromatic system having a hydroxy group in the alpha position, or a five or six membered heterocycle having in the alpha position a heteroatom selected from the group consisting of N, O and S, optionally comprising other N, O or S atoms in their structure, and having from 0-3 double bonds, said aromatic, or heterocyclic system being optionally substituted by up to four substituents independently selected from the group consisting of: phospho, sulfo, halo, carboxy, acetoxy, $C_1$-$C_4$ alkoxy, linear and branched $C_1$-$C_4$ alkyl;

Y is $(CH_2)_n$ or is a xylylene group of formula:

n is an integer selected from 2, 3 and 4,
$R^1$, $R^2$ are independently selected from the group consisting of H, linear or branched $C_1$-$C_4$ alkyl, $C_6$ and $C_{10}$ aryl.

2. The compound according to claim 1, wherein $X^2$ is selected from the group consisting of 2-hydroxyphenyl, 2-hydroxy-naphthyl, 2-furyl, 2-thienyl, 2-pyrrolyl, 2-pyridyl, 4-pyridimidinyl, 2-pyrazinyl optionally substituted by 2 or 1 substituents independently selected from the group consisting of: phospho, sulfo, halogen, $C_1$-$C_4$ alkoxy, carboxy, acetoxy, linear and branched $C_1$-$C_4$ alkyl.

3. The compound according to claim 2, wherein $X^1$ is 2-hydroxyphenyl or 2-hydroxynaphthyl, optionally substituted by 1 or 2 substituents independently selected from the group consisting of methyl and methoxy.

4. The compound according to claim 3, wherein $X^1$ is 2-hydroxyphenyl.

5. The compound according to claim 1, wherein Y is $(CH_2)_n$.

6. The compound according to claim 5, wherein n is 2.

7. A process for preparing a compound of formula (I) as defined in claim 1, which process comprises the step of reducing a compound of formula (II):

(II)

wherein $X^1$, $X^2$ and Y are as defined above, in an appropriate solvent system, in the presence of a reducing agent.

8. The process according to claim 7, further previously comprising the step of preparing said compound of formula (II) by reacting a compound of formula (III) with a compound of formula (IV):

(III)

(IV)

wherein $X^1$, $X^2$ and Y are as defined above, in an appropriate solvent system.

9. A method of forming a chelate comprising reacting a compound of formula (I) as defined in claim 1 with one or more polyvalent metals.

10. A chelate of a compound of the formula (I) as defined in claim 1 with one or more polyvalent metals.

11. A chelate according to claim 10, wherein said polyvalent metal is at least one polyvalent metal from the group consisting of iron, nickel, zinc, manganese, ytterbium, gadolinium, cobalt, copper, palladium, platinum and, gold.

12. The chelate according to claim 11, wherein said polyvalent metal is iron.

13. An agrochemical composition comprising a compound of formula (I) as defined in claim 1 or a polyvalent metal chelate thereof.

14. The agrochemical composition according to claim 13, further comprising a chelating agent selected from the group consisting of ethylene diamine tetraacetic acid (EDTA), diethylene triamine pentaacetic acid (DTPA), N,N'-ethylene-bis(2-hydroxyphenyl)glycine (o,o-EDDHA) and N,N'-ethylene-(2-hydroxyphenyl)-glycinyl-(4-hydroxyphenyl)glycine (o,p-EDDHA).

15. A method of preparing a composition for treating an iron deficiency related plant disease comprising combining a compound as defined in claim 1 or a polyvalent metal chelate thereof with an agriculturally acceptable carrier.

16. The method according to claim 15, wherein said disease is iron chlorosis.

* * * * *